United States Patent [19]
Dobson et al.

[11] Patent Number: 5,743,854
[45] Date of Patent: Apr. 28, 1998

[54] METHOD AND APPARATUS FOR INDUCING AND LOCALIZING EPILEPTIFORM ACTIVITY

[75] Inventors: Jon Paul Dobson; Heinz-Gregor Wieser, both of Zurich, Switzerland; Michael David Fuller, Santa Barbara, Calif.

[73] Assignee: The Regents of the University of California, Oakland, Calif.

[21] Appl. No.: 219,183

[22] Filed: Mar. 29, 1994

[51] Int. Cl.⁶ .......................... A61B 5/0484; A61B 5/05
[52] U.S. Cl. .......................... 600/409; 600/544
[58] Field of Search .......................... 600/13, 9, 15, 600/14, 409, 544; 128/731, 642, 653.1

[56] References Cited

U.S. PATENT DOCUMENTS

| | | | |
|---|---|---|---|
| 3,850,161 | 11/1974 | Liss | 128/731 |
| 4,556,051 | 12/1985 | Maurer | 600/14 |
| 5,092,835 | 3/1992 | Schurig et al. | 600/15 |
| 5,269,746 | 12/1993 | Jacobson | 600/13 |
| 5,323,777 | 6/1994 | Ahonen et al. | 128/731 |
| 5,357,958 | 10/1994 | Kaufman | 600/13 |

FOREIGN PATENT DOCUMENTS

| | | | |
|---|---|---|---|
| 9203185 | 3/1992 | WIPO | 600/13 |

OTHER PUBLICATIONS

Dobson et al, "Evocation of epileptiform activity . . . ", Proceedings of the 9th Inst. Conf. on Biomag., Vienne, Austria 1993.
Dobson et al, "Evocation of epileptiform activity . . . ", EOS, vol. 74, No. 16, Baltimore, MD 1993.

Primary Examiner—Lee S. Cohen
Attorney, Agent, or Firm—Allston L. Jones

[57] ABSTRACT

A method and apparatus for evoking epileptiform activity in patients with drug resistant epilepsy, as part of a presurgical evaluation procedure are disclosed. The apparatus includes a cranial helmet, for generating a DC magnetic field of a sufficient strength to evoke epileptiform activity, and means for localizing the regions of the patient's brain where said epileptiform activity has been evoked. In the preferred embodiment, the magnetic field strength varies between 1 milliTesla and 2 milliTesla, and is generated by two generally similar coils which are coaxially separated, and which are wound on corresponding thermoplastic members to form the helmet. The desired magnetic field strength is produced at about the middle of the distance between the two coils, in general registration with the hippocampus region of the brain. In an exemplary embodiment, the localizing means includes implantable Foramen Ovale electrodes for sensing the evoked and natural epileptic firings. An EEG machine is connected to the Foramen Ovale electrodes, for recording the sensed evoked and natural epileptic firings.

18 Claims, 2 Drawing Sheets

METHOD AND APPARATUS FOR INDUCING AND LOCALIZING EPILEPTIFORM ACTIVITY

BACKGROUND OF THE INVENTION

1. Field of the Invention

The present invention is directed in general to methods for epilepsy diagnosis and treatment, and it more particularly relates to a method and apparatus for evoking and localizing epileptiform activity in patients with drug resistant temporal lobe epilepsy, as part of a presurgical evaluation procedure, by exposing the patient's brain to a DC magnetic field of a predetermined strength.

2. Background Art

There has been numerous reports relating to the sensitivity of animals to magnetic fields, and the recent discovery of magnetite in the human brain has revitalized the question of whether magnetic fields may be hazardous to human beings. The magnetite found in the brain was reported to be similar to that synthesized by certain bacteria and to a number of species in which sensitivity to the geomagnetic field has been demonstrated, Kirschvink, J. L., Jones, D. and MacFadden, B. (Eds), *Magnetite Biomineralization and Magnetoreception in Organisms*, Plenum Publishing Corporation, New York, pp. 682 (1985). In an attempt to clarify whether the human brain is sensitive to magnetic fields, Dubrov, A. P., in *The Geomagnetic Field and Life*, Plenum Publishing Corporation, New York, pp.318 (1978) reviewed the effects of low frequency magnetic fields.

Studies relating to the use of strong pulsed and low frequency AC fields for brain stimulation have been reported by Barker, A. T., Jalinous, R., and Freeston, I. L. in *Non-invasive Magnetic Stimulation of Human Motor Cortex*, Lancet, pp. 1106–1007, (1985) and by Rossini, P. M., Desiato, M. T., Lavaroni, F., and Caramia, M. D., in *Brain Excitability and Electroencephalographic Activation; Non-Invasive Evaluation in Healthy Humans via Transcranial Stimulation*, Brain Research, 567, pp. 111–119, (1991).

Additionally, Wieser, H. G. and Siegel, A. M. in *Analysis of Foramen Ovale Electrode-Recorded Seizures and Correlation with Outcome Following Amygdalohippocampectomy*, Epilepsia, 32(6), pp. 838–850 (1991), report a detailed electroclinical analysis of 320 seizures recorded by Foramen Ovale electrodes in 77 potential candidates for selective temporal lobe surgery because of antiepileptic drug-resistant seizures. In the disclosed procedure, Foramen Ovale (FO) electrodes are fed through the mouth and cheek to the Foramen Ovale.

Conventionally, when treating or diagnosing epileptic patients, particularly drug resistant epileptic patients, electrodes were implanted into the patient's brain for detecting the onset of epileptic seizures. In many cases, the epileptic firings do not commence for a long period, during which time, the electrodes remain implanted and connected to recording instruments, such as electroencephalograph (EEG) machines. Furthermore, the medical staff remain on continuous alert so that when the epileptic firings commence, regions of the brain involved in these epileptic firings may be identified, before surgery can take place.

Such conventional procedures are cumbersome and inconvenient for the patients, and involve significant treatment delays and expenses. It would therefore be desirable to have a new procedure and apparatus for expeditiously evoking and localizing epileptiform activity in drug resistant epileptic patients.

SUMMARY OF THE INVENTION

It is a principal object of the present invention to evoke epileptiform firings in a presurgical evaluation procedure of drug resistant epileptic patients by exposing the patient to a DC magnetic field of between about 1 milliTesla (mT) and 2 mT.

It is another object of the present invention to localize epileptiform areas of the brain, where epileptic seizures are evoked, by using the Foramen Ovale (FO) electrode technique of electroencephalography (EEG), or similar other techniques.

Briefly, the above and further objects and features of the present invention are realized by providing a new method and apparatus for evoking epileptiform activity in patients with drug resistant epilepsy, as part of a presurgical evaluation procedure. The apparatus includes a cranial helmet for generating a DC magnetic field of a desired strength to evoke epileptiform activity, and means for localizing the regions of the patient's brain where said epileptiform activity has been evoked.

In the preferred embodiment, the magnetic field strength varies between 1 milliTesla and 2 milliTeslas, and is generated by two generally similar coils which are coaxially separated, and which are wound on corresponding thermoplastic members to form the helmet, such that the desired magnetic field strength is produced at about the middle of the distance between the two coils, in general registration with the hippocampus region of the brain.

In an exemplary embodiment, the localizing means includes implantable Foramen Ovale electrodes for sensing the evoked and natural epileptic firings. An EEG machine is connected to the Foramen Ovale electrodes, for recording the evoked and natural epileptic firings. One or more surface electrodes can be externally positioned on the patient's head, for non-invasively sensing the evoked and natural epileptic firings. As an alternative to EEG's which require electrode implantation or surface electrodes, the evoked and natural epileptic firings could be recorded non-invasively, i.e., remotely, be an MEG machine, without touching the patient's body. This is possible due to the delay in response to the fields which will enable MEG recording. This method should also prove useful in research efforts aimed at determining the influence of environmental magnetic fields on the central nervous system function.

The evocation and localization of epileptiform activity is carried out by applying DC magnetic fields of between 20 and 100 times the strength of the geomagnetic field, such as between 1 mT and 2 mT, using the Foramen Ovale electrode technique of electroencephalography. The activity relating to the magnetic field is distinguished from background levels by comparing the number of events in the ten second intervals before and after the field application.

The application of the DC magnetic field and the subsequent epileptic firings permit the rapid identification of the epileptiform areas of the brain, by means of an EEG. In some cases, this evoked epileptiform activity has proven to provide important data, particularly when no natural activity is observed. In other cases, natural epileptiform firings showed that the same regions of the brain were involved in both natural and evoked firings.

Eventually, it is expected that the magnetoencephalography (MEG) techniques will develop sufficiently, so as to replace the invasive electrode implantation, and hence will render the present invention totally non-invasive.

BRIEF DESCRIPTION OF THE DRAWINGS

The above and other features of the present invention and the manner of attaining them, will become apparent, and the invention itself will be best understood, by reference to the following description and the accompanying drawings, wherein.

DETAILED DESCRIPTION OF THE PREFERRED EMBODIMENT

Figure 1:
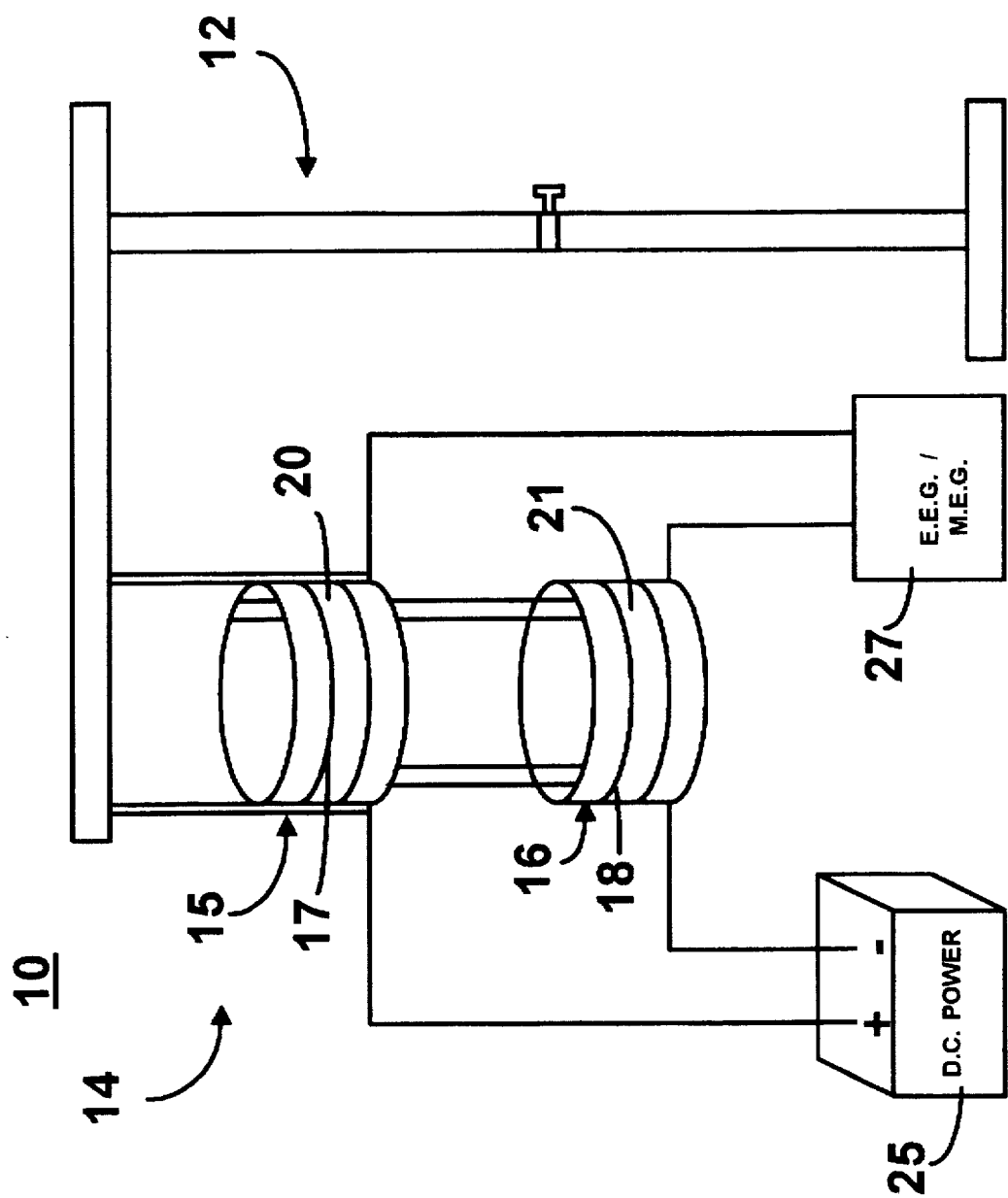
FIG. 1 is a schematic view of an apparatus for evoking and localizing epileptiform activity according to the present invention, by applying a DC magnetic field of a predetermined strength.

Referring now to the drawings and more particularly to FIG. 1 thereof, there is illustrated an apparatus 10 for evoking epileptiform activity, and for localizing corresponding epileptic firings in epileptic patients, and particularly in drug resistant epileptic patients. As used herein, an "epileptic firing" refers to the expression on a EEG record of nervous activity associated with epilepsy. The voltages observed during epileptic seizures include spiky EEG waveforms, paroxysmal depolarization shifts (PDS), which were evoked with the application of the magnetic field. The evoked epileptic firings are generally found to occur in the same location as the natural epileptic firings exhibited by the patients.

The apparatus 10 generally includes a telescoping aluminum support system 12 for adjustably retaining a cranial helmet 14 around a patient's head (not shown). The helmet 14 includes a pair of generally similar coaxial coils 15, 16 that are spaced apart by a predetermined distance, such that the helmet 14 generates the a DC magnetic field having a desired strength. Each coil 15, 16 includes a length of copper wire 17, 18 wound several times around a respective cylindrically shaped thermoplastic frame 20, 21.

The coils 15 and 16 are connected to the positive and negative poles of a DC power source 25 for generating a DC magnetic field through the helmet 14. When the helmet 14 is placed around the patient's head, the generated magnetic field varies across the patient's head by as much as 10 percent to 20 percent. However, the desired magnetic field is applied within the region of the hippocampus. As used herein, the "hippocampus" is a region of the brain which appears to be a part of the primitive limbic system, and which plays a role in memory and various regulatory aspects of the body.

The helmet 14 generates the desired magnetic strength at about the middle of the distance between the two coils 15 and 16. It has been experimentally found that the evocation and localization of epileptiform activity is accomplished by applying a DC magnetic field of between 20 and 100 times the strength of the geometric field, such as between 1 mT and 2 mT. Evoked responses were recorded using the Foramen Ovale electrode technique of encephalography. As used herein, "Geomagnetic field" refers to the earth magnetic field, which is generated in the molten iron nickel outer core of the earth. The strength of the geomagnetic field varies between about 0.03 mT at the equator and about 0.07 mT at the poles. The threshold effect of the observation for the epileptic firing is 0.9 mT, which is about 20 times the average geomagnetic field strength. Magnetic fields of such strength have been recorded in the vicinity of some household appliances, however, those fields are different in that they are alternating fields.

The localization of the epileptic activity in the human brain of epileptic patients with drug resistant temporal lobe epilepsy undergoing preoperative evaluation, is carried out by using Foramen Ovale electrodes technique, as described by Wieser, H. G., in *Semi-Invasive EEG: Foramen Ovale Electrodes, Epilepsy Surgery*, H. Luders, Ed., pp. 361–370, (Raven Press, New York, 1991). Electrodes are inserted via the Foramen Ovale (FO) to record the epileptiform activity from the region of the hippocampus. In order to induce the epileptiform activity, the patient is subjected to a DC magnetic field in the order of few milliTeslas, by means of the helmet 14.

Each of the inserted Foramen Ovale electrodes includes four TEFLON-insulated, helically-wound silver wires having a diameter of about 4.5 mils in four poles, and are mounted on a stainless steel wire 0.1 mm in diameter. However, it should be understood to one skilled in the art, after reviewing the present invention that other sensing and localization techniques can alternatively be used, without departing from the scope of the present invention.

For this purpose, an EEG machine and/or an MEG machine 28 can also be connected to the Foramen Ovale electrodes and to surface electrodes (not shown), for recording the evoked and natural epileptic firings. An exemplary EEG machine 27 used in the apparatus 10 of the present invention, is a Nihon Kohden, Neurofax 44218, and the timing of the magnetic field changes was recorded by a voltage proportional to the magnetic field, on an additional channel.

Figure 2:
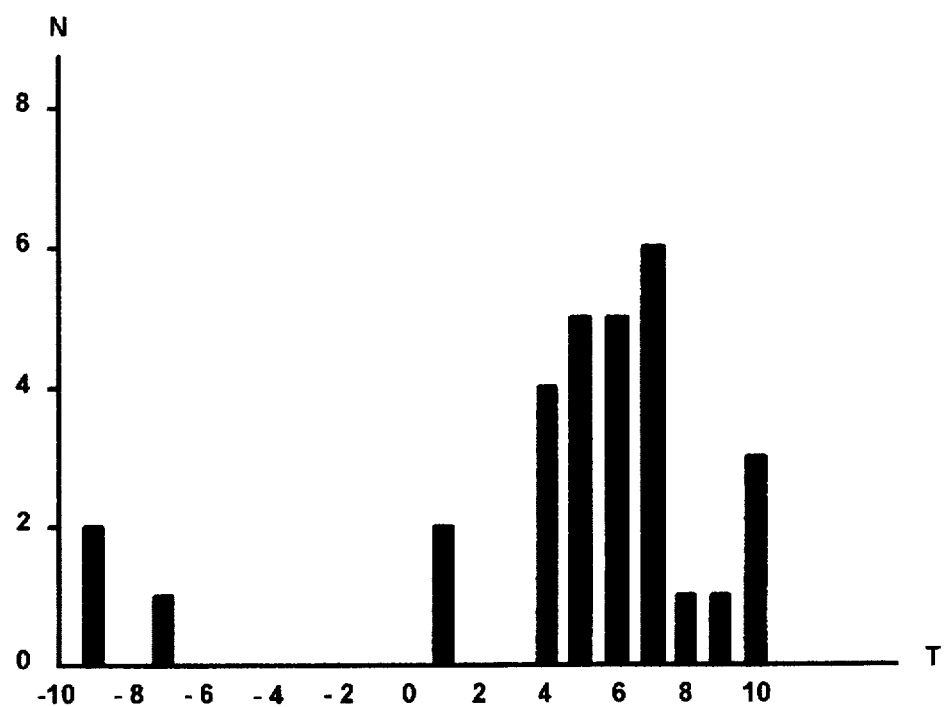
FIG. 2 is an exemplary graph showing the number (N) of epileptic events ten seconds before and after the application of the magnetic field.
Figure 3:
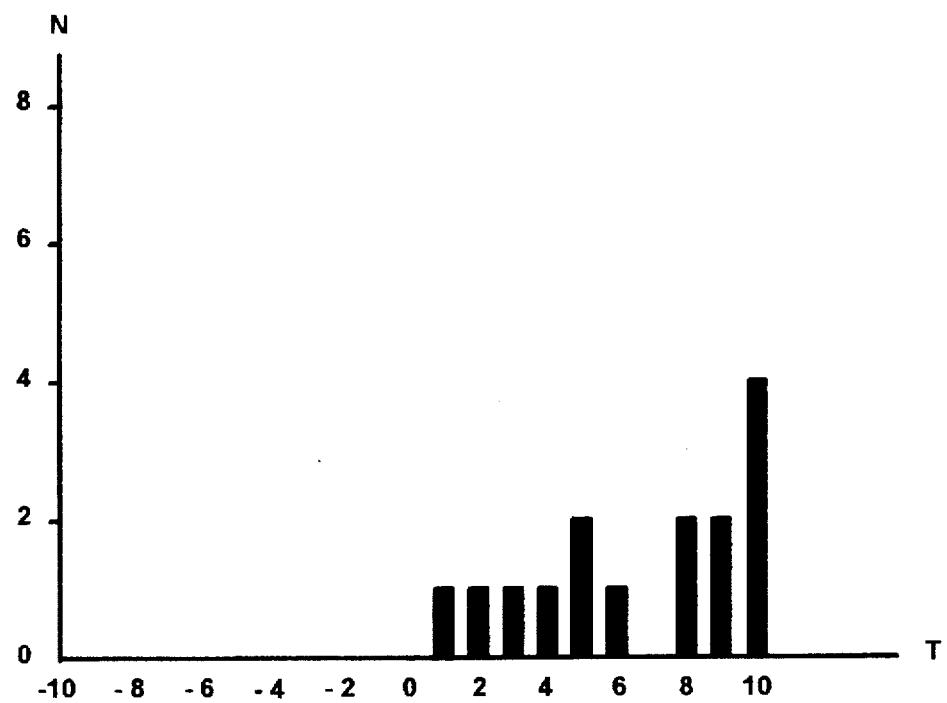
FIG. 3 is another exemplary graph showing the number (N) of epileptic events ten seconds before and after the application of the magnetic field in a second patient.

As illustrated by FIGS. 2 and 3, the activity relating to the magnetic field is distinguished from the background levels, by applying a filter and comparing the number of events in the ten seconds intervals before and after the application of the magnetic field, leading to the following observations: The evocation of epileptiform activity by the magnetic fields between 1 mT and 2 mT was experimentally observed. In a particular test, single or multiple events were observed within the ten seconds following the application of the magnetic field in 9 out of 12 tests. Weaker DC magnetic fields below 0.9 mT did not evoke the epileptiform activity. Furthermore, it has been found that the epileptiform activity might be delayed before evocation, for a few seconds or longer, in the hippocampal formation, which is the primary epileptogenic zone. When a non-epileptic patient was subjected to the DC magnetic field treatment, no enhanced activity was recorded by the surface electrode EEG.

The ability to evoke epileptiform activity with magnetic fields facilitates the localization of the primary epileptogenic focus in epileptic patients. Eventually, due to the delay in response, magnetoencephalography (MEG) might be used which could provide a non-invasive technique for localizing epileptiform activity.

Using the apparatus 10, the site of the evoked activity was established and, in some cases, subsequent amigdyl-hippocampectomy eliminated the patients' seizures. Surface electrodes were also monitored and, in some cases, some activity was observed on these channels. The experiments were repeated on non epileptic subjects with surface electrodes only, and no anomalous activity was observed.

The evocation of epileptiform activity by relatively weak magnetic fields, i.e., in the range of 1 mT to 2 mT addresses the possibility that magnetic fields which might trigger such activity should not be totally discounted, and in certain circumstances, it should be guarded against. Therefore, the present invention serves as an indication that it might be useful to shield DC magnetic fields in the range of 1 mT and 2 mT, and in order to prevent the accidental triggering of epileptic seizures in epilepsy prone individuals.

While particular embodiments of the present invention have been disclosed, it is to be understood that various different modifications are possible and are contemplated within the scope of the specification, drawings, abstract and appended claims. In particular, the operation of the helmet 14 can be automated and computer controlled.

What is claimed is:

1. An apparatus for evoking epileptiform activity in a patient with drug resistant epilepsy, as part of a presurgical evaluation procedure, the apparatus comprising in combination:

a DC magnetic field generator adapted to surround at least part of the patient's head, to generate a DC magnetic field of a strength sufficient to evoke epileptiform activity in the head of said patient;

a DC power source coupled to said DC magnetic field generator;

a support structure to maintain said DC magnetic field generator in a selected location relative to said patient's head; and sensors adapted to be coupled to said patient's head to monitor said epileptiform activity in the patient's head and to assist in the location selection of said DC magnetic field generator to evoke said epileptiform activity in said patient's head.

2. The apparatus according to claim 1, wherein said magnetic field strength varies between about 1 milliTesla and 2 milliTesla.

3. The apparatus according to claim 2, wherein said DC magnetic field generator includes two or more coils, each of which is wound around a corresponding thermoplastic member.

4. The apparatus according to claim 3, wherein said support structure maintains said DC magnetic field generator at a location to locate the production of said magnetic field within the hippocampus region of the brain.

5. The apparatus according to claim 4, wherein said coils and said corresponding thermoplastic members form a helmet which is adapted to be placed around at least part of a patient's head.

6. The apparatus according to claim 2, wherein said DC magnetic field generator includes two identical coils which are separated by a predetermined distance having a midpoint bisecting said predetermined distance, such that said desired magnetic field strength is produced at about the middle of said predetermined distance between said two coils.

7. The apparatus according to claim 1, wherein said sensors comprise Foramen Ovale electrodes adapted to be implanted to sense evoked and natural epileptic firings.

8. The apparatus according to claim 7, further including an electroencephalogram (EEG) machine, connected to said Foramen Ovale electrodes, for recording sensed evoked and natural epileptic firings.

9. The apparatus according to claim 8, further including one or more surface electrodes adapted to be externally positioned on the patient's head, for non-invasively sensing evoked and natural epileptic firings.

10. The apparatus according to claim 9, further including a magnetoencephalography (MEG) machine, connected to said surface electrodes, for recording the evoked and natural epileptic firings.

11. A method for evoking epileptiform activity in a patient with drug resistant epilepsy, as part of a presurgical evaluation procedure, the method comprising the steps of:

(a) generating a DC magnetic field of a desired strength around at least part of the patient's head;

(b) selecting said desired magnetic field strength so as to evoke epileptiform activity; and (c) localizing the regions of the patient's brain where said epileptiform activity is evoked.

12. The method according to claim 11, wherein said step of selecting includes varying said magnetic field strength between 1 milliTesla and 2 milliTesla.

13. The method according to claim 12, wherein said step of generating includes using two generally identical coils, each of which is wound around a corresponding thermoplastic member, and wherein said coils are separated by a predetermined distance, such that said desired magnetic field strength is produced about the midpoint of said predetermined distance between said two coils.

14. The method according to claim 13, further including the step of registering said desired magnetic field strength with the hippocampus region of the brain.

15. The method according to claim 11, wherein said step of localizing includes implanting Foramen Ovale electrodes to sense evoked and natural epileptic firings.

16. The method according to claim 15, further including the step of connecting an electroencephalogram (EEG) machine, to said Foramen Ovale electrodes, for recording the sensed evoked and natural epileptic firings.

17. The method according to claim 16, further including the step of positioning one or more surface electrodes externally on the patient's head, for non-invasively sensing the evoked and natural epileptic firings.

18. The method according to claim 17, further including the step of connecting a magnetoencephalography (MEG) machine, to said surface electrodes, for recording the evoked and natural epileptic firings.

* * * * *